United States Patent [19]

Dormoy

[11] Patent Number: 5,420,300

[45] Date of Patent: May 30, 1995

[54] SUBSTITUTED 2-ETHYLBENZO [B] THIOPHENE, PROCESS FOR PREPARATION THEREOF AND USE THEREOF AS SYNTHETIC INTERMEDIATE

[75] Inventor: Jean-Robert Dormoy, Sisteron, France

[73] Assignee: Elf Sanofi, Paris, France

[21] Appl. No.: 122,677

[22] Filed: Sep. 17, 1993

[30] Foreign Application Priority Data

Sep. 22, 1992 [FR] France ................................ 92 11276

[51] Int. Cl.⁶ .................. C07D 333/52; C07D 333/54
[52] U.S. Cl. .......................................... 549/49; 549/58
[58] Field of Search ...................... 549/49, 58

[56] References Cited

U.S. PATENT DOCUMENTS 3,629,267 12/1971 Kaiser et al. ........................ 549/49
4,737,516 4/1988 Stütz ..................................... 549/49

FOREIGN PATENT DOCUMENTS 0279263 8/1988 European Pat. Off. .
0281254 9/1988 European Pat. Off. .
0345592 12/1989 European Pat. Off. .

OTHER PUBLICATIONS

Donald S. Noyce et al., "Reactivity of Benzo[b]thiophene in electrophilic Reactions as Determined from Solvolysis Rates", Journal of Organic Chemistry, vol. 39, No. 19, 1974, pp. 2828–2831.

Chem. Abs, CA95(9): 80622d, Chatterjee et al., 1981.

*Primary Examiner*—Richard L. Raymond
*Assistant Examiner*—Deborah Lambkin
*Attorney, Agent, or Firm*—Jacobson, Price, Holman & Stern

[57] ABSTRACT

The subject of the invention is 2-(1-bromoethyl)benzo[b]thiophene of formula:

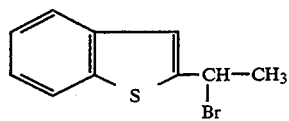

as well as a process for the preparation thereof, characterised in that 2-ethylbenzo[b]thiophene is reacted, in a solvent, with a brominating agent in the presence of a free radical initiator, which provides the desired compound, and the use thereof in the preparation of 2-(1-(benzyloxyamino)ethyl)benzo[b]thiophene and of N-hydroxy-N-{1-(benzo[b]thien-2-yl)ethyl}urea.

No figure.

1 Claim, No Drawings

SUBSTITUTED 2-ETHYLBENZO [B] THIOPHENE, PROCESS FOR PREPARATION THEREOF AND USE THEREOF AS SYNTHETIC INTERMEDIATE

The present invention relates, in a general way, to a new substituted 2-ethylbenzo[b]thiophene, to the process for the preparation thereof and to the use thereof as a synthetic intermediate.

More precisely, the subject of the invention is 2-(1-bromoethyl)benzo[b]thiophene of formula:

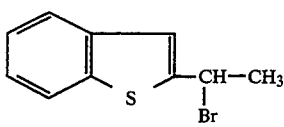

I

The compound of the invention has proved to be particularly useful as an intermediate product, especially for the preparation of N-substituted 2-(1-aminoethyl)benzo[b]thiophenes, especially 2-(1-(benzyloxyamino)ethyl)benzo[b]thiophene.

The latter compound can itself be used as an intermediate in the preparation of various products, especially for the final synthesis of N-hydroxy-N-{1-(benzo[b]thien-2-yl)ethyl}urea of formula:

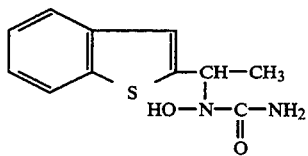

Ia

This substituted urea, which was described in Patent Application EP-0,279,263, has proved to be particularly advantageous for its pharmacological properties, especially its leukotriene-inhibiting properties, which can make it useful in the field of asthma, rheumatoid polyarthritis and inflammatory diseases of the colon.

Several synthetic routes to the compound of formula Ia were described in the abovementioned Patent Application EP-0,279,263.

One of them involves the sequence of the following reaction steps:

a) heating 2-(1-chloroethyl)benzo[b]thiophene with O-benzylhydroxylamine in a solvent such as dimethyl sulphoxide or tetrahydrofuran to give 2-(1-(benzyloxyamino)ethyl)benzo[b]thiophene of formula:

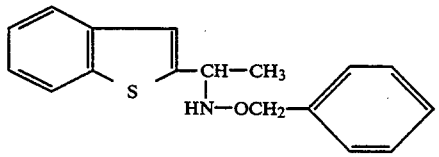

II b) reacting the benzyloxy-substituted compound thus formed with trimethylsilyl isocyanate to give N-benzyloxy-N-{1-(benzo[b]thien-2-yl)ethyl}urea;

c) catalytic hydrogenation of this substituted urea over palladium-on-charcoal to finally obtain the compound of formula Ia.

However, no example describes the use of this process so as to be able to judge its feasibility on the industrial level.

Moreover, no method was reported in this patent application for the preparation of the starting compound, namely 2-(1-chloroethyl)benzo[b]thiophene.

This chlorine-substituted compound is, however, a known compound, having been described in J. Org. Chem., 1974, 39 (18), pp. 2823–2831, as well as a process for its preparation.

According to this process, 2-(1-chloroethyl)benzo[b]thiophene is obtained with a yield of 80% after treatment of 2-(1-hydroxyethyl)benzo[b]thiophene by means of thionyl chloride, this alcohol being itself prepared with a yield of 44% from benzo[b]thiophene. Consequently, 2-(1-chloroethyl)benzo[b]thiophene could be obtained by use of this process according to a maximum overall yield of 35%.

In the context of developing the invention, an attempt was made to prepare 2-(1-(benzyloxyamino)ethyl)benzo[b]thiophene by reacting 2-(1-chloroethyl)benzo[b]thiophene and O-benzylhydroxylamine according to the reaction scheme of the abovementioned European Patent Application.

This product could be synthesized with yields, however, not exceeding 57%.

The search for an industrial process for the preparation of 2-(1-(benzyloxyamino)ethyl)benzo[b]thiophene, using synthetic intermediates which are easily accessible and inexpensive, as well as a satisfactory yield of final product, remains of indisputable interest.

Now, it has been found, in an entirely surprising way, according to the invention, that 2-(1-bromoethyl)benzo[b]thiophene can provide access to the compound of formula II with ease and with very good yields, the yields obtained being of the order of 75%.

Moreover, it was found that 2-(1-bromoethyl)benzo[b]thiophene can itself be obtained more advantageously than the corresponding 1-chloro substituted compound, and with yields greater than the latter.

According to the invention, 2-(1-bromoethyl)benzo[b]thiophene is prepared by reacting 2-ethylbenzo[b]thiophene with a brominating agent in a suitable solvent in the presence of a free radical initiator.

Generally, N-bromosuccinimide or 1,3-dibromo5,5-dimethylhydantoin is used as the brominating agent and azobisisobutyronitrile is used as the free radical initiator.

Moreover, the reaction preferably takes place at a temperature between room temperature and the reflux temperature of the mixture.

A non-polar solvent such as, for example, carbon tetrachloride, cyclohexane or heptane is generally used as the solvent.

As for the starting 2-ethylbenzo[b]thiophene, it is a known product, widely described in the chemical literature.

As shown above, it was found that the 2-(1-bromoethyl)benzo[b]thiophene of the invention shows a number of advantages over its chlorinated homologue, related to its preparation process on the one hand and its use as a synthetic intermediate for the preparation of the benzyloxy-substituted compound of formula II on the other hand.

These advantages could be deduced from various comparative tests carried out in the context of the development of the present invention.

For example, 2-(1-bromoethyl)benzo[b]thiophene and its 1-chloro homologue were prepared according to a strictly analogous process consisting in reacting 1 molar milliequivalent of 2-ethylbenzo[b]thiophene in 13 volumes of heptane with 0.55 molar milliequivalent of halogenating agent, that is to say 1,3-dibromo-5,5-dimethylhydantoin or 1,3-dichloro-5,5-dimethylhydantoin, in the presence of X % of azobisisobutyronitrile (AIBN) at a temperature T and for a reaction time of Y hours.

This reaction, pictured below, provided a mixture of various products, namely compounds A to D below:

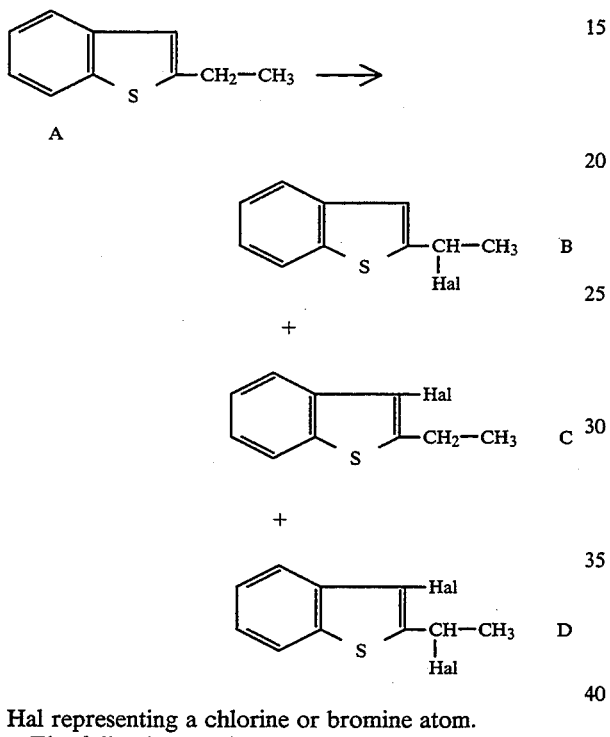

Hal representing a chlorine or bromine atom.
The following results were obtained:

| Hal | AIBN (%) | T (°C.) | Y (h) | % Compounds | | | |
|---|---|---|---|---|---|---|---|
| | | | | A | B | C | D |
| Br | 1 | 60 | 2 | 5–7 | 80–83 | 3–5 | 2–4.5 |
| Cl | 5 | 60 then 70 | 2 then 7 | 20–24 | 37 | 37–43 | — |

These results show that the selectivity of the conversion of 2-ethylbenzo[b]thiophene to the α-halogenated compound is greater in the case of the bromination. This selectivity is expressed by 2-(1-bromoethyl)benzo[b]thiophene yields of more than 80%, in comparison with: 2-(1-chloroethyl)benzo[b]thiophene yields of less than 40%.

Additionally, the use of a greater amount of AIBN is shown to be necessary for the chlorination.

As shown above, 2-(1-bromoethyl)benzo[b]thiophene can lead to the benzyloxy-substituted compound of formula II.

Consequently, another subject of the invention relates to the preparation of 2-(1-(benzyloxyamino)ethyl)-benzo[b]thiophene by using a process according to which 2-(1-bromoethyl)benzo[b]- thiophene is reacted with O-benzylhydroxylamine.

Generally, this reaction takes place at room temperature and in a polar solvent such as tetrahydrofuran, N,N-dimethylformamide, dimethyl sulphoxide or acetonitrile.

Comparative tests have made it possible to reveal the superiority of the 1-bromo substituted compound of formula I over its 1-chloro homologue in the preparation of 2-(1-(benzyloxyamino)ethyl)benzo[b]thiophene. To this end, 1 molar equivalent of 2-(1-bromoethyl)-benzo[b]thiophene or of 2-(1-chloroethyl)benzo[b]thiophene was reacted with Z molar equivalents of O-benzylhydroxylamine in tetrahydrofuran at a temperature $T_1$ for Y1 hours.

This reaction, pictured below, made it possible to obtain compound E or the desired compound:

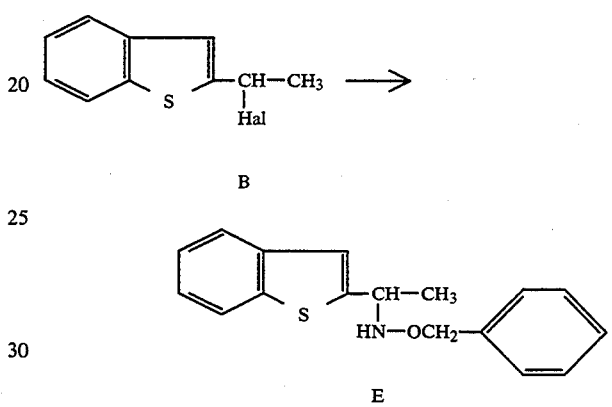

Hal denoting a chlorine or bromine atom.
The following results were recorded:

| Hal | Z | $T_1$ (°C.) | $Y_1$ (h) | Compound E | |
|---|---|---|---|---|---|
| | | | | %* | %** |
| Br | 2,2 | 30 to 40 | 7 to 10 | 73 to 78 | 70 to 76 |
| Cl | 3 | 20 then 60 | 12 12 | 60 to 65 | 55 to 58 |

*estimation by liquid phase chromatography

**after isolation by silica gel chromatography

These results show that the use of the chlorinated compound B to prepare the desired compound E requires harsher reaction conditions which are reflected by a prolonged heating at 60° C. in place of 30° to 40° C. in the case of the corresponding brominated compound B.

Moreover, in comparison with the brominated compound B, the chlorinated compound B leads to a lower yield of compound E with an increase in the level of by-products.

As mentioned above, 2-(1-bromoethyl)benzo[b]thiophene can also be used for preparing N-hydroxy-N-{1-(benzo[b]thien-2-yl)ethyl}urea of formula Ia.

Consequently, the invention relates to 2-(1-bromoethyl)benzo[b]thiophene as an intermediate in the final synthesis of the substituted urea of formula Ia.

For example, it is possible to prepare this substituted urea of formula Ia starting from the benzyloxy-substituted compound of formula II, itself obtained according to the invention from 2-(1-bromoethyl)benzo[b]thiophene, by implementing a process comprising the following steps:

a) the benzyloxy-substituted compound of formula II is first treated with trimethylsilyl isocyanate in a suitable solvent, such as a polar solvent, for example an ether, and at the reflux temperature of the mixture, and then with an aqueous ammonium chloride solution to produce N-benzyloxy-N-{1-(benzo[b]thien-2-yl)ethyl}urea;

b) this substituted urea is hydrogenated in the presence of a catalyst such as palladium-on-charcoal, optionally in the presence of ammonium formate, in a suitable solvent such as acetic acid and at a temperature of 20° to 50° C. to finally produce the desired compound of formula I.

The following non-limiting examples illustrate the invention:

EXAMPLE 1

Preparation of 2-(1-bromoethyl)benzo[b]thiophene

A solution of 9.78 g (60 mmol) of 2-ethylbenzo[b]thiophene in 10 ml of heptane is added, over 10 minutes, to a mixture of 9.43 g (33 mmol) of 1,3-dibromo-5,5-dimethylhydantoin and 0.49 g (3 mmol) of azobisisobutyronitrile in 117.5 ml of heptane preheated to 60° C. The mixture is maintained for 1 additional hour at this temperature. After cooling to 20° C., stirring is continued for 1 hour and then the 5,5-dimethylhydantoin which has precipitated is filtered off and washed with 10 ml of heptane. The filtrate is washed with an aqueous sodium thiosulphate solution (3 g/100 ml) and then with 3 times 100 ml of water. After drying over sodium sulphate, the heptane phase is concentrated to approximately 40 ml and then cooled to $-10°$ C. for one hour and a half. The precipitate formed is filtered off and dried under partial vacuum at 20° C. to provide 9.05 g of the desired compound in the form of a beige powder, which represents a yield of 57% (M.p.: 53° C., purity by liquid phase chromatography: 92%). A second, less pure sample is obtained by concentrating the mother liquors (16%).

In this way, 2-(1-bromoethyl)benzo[b]thiophene is obtained with a yield of 73%. $^1$H N.M.R. spectrum (CDCl$_3$, 300 MHz): 2.18 (d, J=6.7 Hz, 3H, CH$_3$) 5.57 (q, J=6.7 Hz, 1H, CHBr) 7.25–7.45 (m, 3H,, aromatic protons) 7.65–7.85 (m, 2H,, aromatic protons) $^{13}$C N.M.R. spectrum (CDCl$_3$, 75 MHz): 27.65 (CH$_3$), 43.69 (CHBr), 121.74, 122.54, 123.99, 124.68, 125.02 (5 CH, aromatic carbons), 139.01, 139.73, 148.02 (3C, quaternary aromatic carbons).

EXAMPLE 2

Preparation of N-hydroxy-N-{1-(benzo[b]thien-2-yl)ethyl}urea a) 2-(1-(benzyloxyamino)ethyl)benzo[b]thiophene:
1 g (4mmol) of 2-(1-bromoethyl)benzo[b]thiophene (purity: 97%) and 1.48 g (12 mmol) of O-benzylhydroxylamine are dissolved, under a nitrogen atmosphere, in 2 ml of anhydrous tetrahydrofuran. The mixture is stirred for 5.5 hours at 20° C. After addition of 15 ml of water, the reaction mixture is acidified to pH=3 with dilute hydrochloric acid and extraction is carried out with 4 times 15 ml of diethyl ether. The ether phase is dried over sodium sulphate and concentrated under reduced pressure, which gives 1.44 g of a brown oil. Filtration is then carried out through a silica gel column (eluent:1/99 to 30/70 gradient of dichloromethane in hexane).

In this way, 0.89 g of 2-(1-(benzyloxyamino)ethyl)-benzo[b]thiophene is obtained in the form of a pink-beige solid. M.p.: 55°–56° C. Yield: 76% $^1$H N.M.R. spectrum (CDCl$_3$, 300 MHz): 1.59 (d, J=6.6 Hz, 3H, CH$_3$CH) 4.58 (q, J =6.6 Hz, 1H, CHCH$_3$) 4.83 (s, 2 H, CH$_2$, phenyl) 5.75 (broad s, 1H, NH) 7.26–7.50 (m, 8H, aromatic protons) 7.78–7.92 (m, 2H, aromatic protons) $^{13}$C N.M.R. spectrum (CDCl$_3$, 75 MHz): 20.31 (CH$_3$), 56.78 (CHN), 76.87 (CH$_2$-phenyl), 120.89, 122.36, 123.25, 123.94, 124.08, 127.80 (6 CH, aromatic carbons), 128.32 and 128.52 (2C ortho+2C meta of CH$_2$-phenyl), 137.69, 139.36, 139.51, 147.77 (4C, quaternary aromatic carbons).

b) N-benzyloxy-N-{1-(benzo[b]thien-2-yl)ethyl}urea
10.1 g (33.6 mmol) of 2-(1-(benzyloxyamino)ethyl)-benzo[b]thiophene (purity approximately 94%) and 12.5 g (3.3 mol equiv) of trimethylsilyl isocyanate are dissolved in 25 ml of tetrahydrofuran. The mixture is heated at reflux for 48 hours.

After cooling to 25° C., 150 ml of a saturated aqueous ammonium chloride solution are added, stirring is carried out for 1 hour and the mixture is extracted with two times 50 ml of ethyl acetate. The organic phases are combined and washed with two times 25 ml of water. The combined organic phases are dried over sodium sulphate and evaporated to dryness and the residue is purified by silica gel chromatography.

In this way, 5.9 g of N-benzyloxy-N-{1-(benzo[b]-thien-2-yl)ethyl}urea are obtained in the form of a cream powder. M.p.: 126° C. Yield: 54 % I.R. spectrum (KBr): 3420 (NH$_2$), 1661 (C=O) $^1$H N.M.R. spectrum (300 MHz, d$_6$-DMSO): 1.6 (d, J=7 Hz, 3H, CH$_3$) 4.65–4.85 (m, 2H, OCH$_2$) 5.55 (q, J=7 Hz, 1H, CHCH$_3$) 6.7 (broad s, 2H, NH$_2$) 7.2–7.5 (m, 8H, aromatic protons) 7.70–7.95 (2m, 2H, aromatic protons) $^{13}$C N.M.R. spectrum (75 MHz, d$_6$-DMSO): 17.68 (CH$_3$), 53.91 (CHN), 78.03 (OCH$_2$), 121.95, 122.25, 123.41, 124.21, 124.25, 128.22, 128.30 (×2), 129.15 (×2) (10 CH, aromatic carbons), 135.47, 138.92, 138.96, 145.28 (4C, quaternary aromatic carbons).

c) N-hydroxy-N-{1-(benzo[b]thien-2-yl)ethyl}urea
2.08 g (6 mmol) of N-benzyloxy-N-{1-(benzo[b]-thien-2-yl)ethyl}urea (purity approximately 94%), 1 g of 10% palladium-on-charcoal, 62.5 ml of glacial acetic acid and 6 drops of 12N hydrochloric acid are introduced into a reactor.

The mixture is maintained for 24 hours at 50° C. under a hydrogen pressure of 5 bar. After cooling, filtering off the catalyst through diatomaceous earth, neutralizing with sodium hydroxide, extracting with ethyl acetate and evaporating the solvent, the residue is purified by silica gel chromatography (eluent:50/50 to 100/0 gradient of ethyl acetate in hexane).

In this way, 0.16 g of N-hydroxy-N-{1-(benzo[b]-thien-2-yl)ethyl}urea is obtained in the form of a beige solid. M.p.: 154° C. Yield: 11% I.R. spectrum (KBr) : 3475 (NH$_2$), 1666 (C=O) $^1$H N.M.R. spectrum (300 MHz, d$_6$-DMSO): 1.51 (d, J=7.1 Hz, 3H, CH$_3$), 5.56 (q, J=7.1 Hz, 1H, CH-CH$_3$), 6.45 (broad s, 2H, NH$_2$), 7.25–7.45 (m, 3H, aromatic protons), 7.70–7.95 (m, 2H, aromatic protons), 9.27 (s, 1H, OH) Mass spectrum (CI-CH$_4$): 237 (MH)$^+$, 251 (MCH$_3$)$^+$, 265 (MC$_2$H$_5$)$^+$
I claim:
1. 2-(1-Bromoethyl)benzo[b]thiophene of formula:
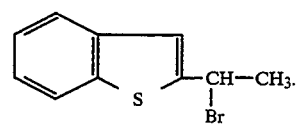
* * * * *